United States Patent [19]

Merianos et al.

[11] 4,155,994

[45] May 22, 1979

[54] HAIR CONDITIONING AGENTS

[75] Inventors: John J. Merianos, Jersey City, N.J.;
Harold A. Green, Havertown, Pa.;
Morris Weinstein, Paramus, N.J.

[73] Assignee: Kewanee Industries, Inc., Bryn Mawr, Pa.

[21] Appl. No.: 761,320

[22] Filed: Jan. 21, 1977

[51] Int. Cl.$^2$ .................. A61K 7/06; A61K 7/08
[52] U.S. Cl. ......................... 424/70; 252/316;
252/317; 424/DIG. 2; 424/78; 424/168
[58] Field of Search ............ 424/70, 78, 168, DIG. 2; 252/316, 317

[56] References Cited

U.S. PATENT DOCUMENTS

| | | | |
|---|---|---|---|
| 3,778,476 | 12/1973 | Rembaum et al. | 424/78 X |
| 3,874,870 | 4/1975 | Green et al. | 424/78 X |
| 3,923,973 | 12/1975 | Green et al. | 424/78 |
| 3,929,990 | 12/1975 | Green et al. | 424/78 |
| 3,966,904 | 6/1976 | Green et al. | 424/78 |
| 3,980,091 | 9/1976 | Dasher et al. | 424/70 X |

*Primary Examiner*—James O. Thomas, Jr.
*Assistant Examiner*—Vera C. Clarke
*Attorney, Agent, or Firm*—Arthur A. Jacobs

[57] ABSTRACT

A hair conditioning agent comprising the condensation product of 1,4-dichloro-2-butene and 1,4-bis-dimethylamino-2-butene.

4 Claims, No Drawings

HAIR CONDITIONING AGENTS

This invention relates to a water-soluble hair conditioning agent, and it more particularly relates to a non-toxic, non-irritating, water-soluble hair conditioning agent having quaternary ammonium moieties as part of the linear chain rather than as mere appendages thereto.

Although many hair conditioning agents are on the market, they are generally subject to one or more disadvantages. For example, they may not be adequately water-soluble, or they may not be sufficiently non-toxic or non-irritating, or they may not be sufficiently substantive to the hair, or they may not be sufficiently compatible with detergents of the type that are usually used in washing the hair.

In accordance with the present invention, all of the aforesaid disadvantages are overcome by using as a hair conditioner a water soluble linear polyquaternary ammonium product formed by condensing 1,4-dichloro-2-butene with 1,4-bis-dimethylamino-2-butene in molar ratios of about 1:2 to about 2:1.

The synthesis of the product of this invention has been fully disclosed in U.S. Pat. No. 3,874,870, dated Apr. 1, 1975, the disclosure of which is incorporated herein by reference.

The present product is substantially non-toxic. In this respect, a 40% aqueous solution has been found to have an "LD-50" of between 4.28 ml. and 8.4 ml. per kilogram of body weight, as determined in accordance with the method of Litchfield, and Wilcoxon, described in the "Journal of Paramacology and Experimental Therepeutics", Vol. 96, pg. 99, 1949. Based on a density of 1.15 for the 40% aqueous solution, the "LD-50" is 1.9 grams to 3.9 grams of pure active material per kilogram of body weight. These results show sufficient lack of toxicity for the purposes of the present invention.

A 40% aqueous solution is also non-irritating to the skin and is not a primary irritant. This evaluation was made in accordance with the method of Draize, as described in "Appraisal of the Safety of Chemicals in Food, Drugs, and Cosmetics", published by the Association of Food and Drug Officials of the United States.

The product of the present invention is also non-irritating to the eyes when applied directy to the eyes in aqueous concentrations of 4%, in accordance with the method of Draize as described in the aforesaid "Approval of the Safety of Chemicals in Foods, Drugs, and Cosmetics."

The product's efficiency as a hair conditioner is shown by the fact that in concentrations as low as ½ of of 1% it imparts a smooth feeling to hair, and in concentrations as low as 1%, it promotes easy detangling of hair, and facilitates hair combing by eliminating or diminishing "drag".

When properly formulated into a cream rinse or shampoo, the product is highly substantive to hair; but, more importantly, even with successive rinsing and shampooing, there is no noticable buildup of insoluble solid matter on the hair, as is the case with most hair-conditioning agents, especially those which comprise water-insoluble, high molecular weight polymers.

A maximum adsorption of the product of this invention on the hair is reached almost immediately, after which no further deposit occurs. Consequently, there is no unsightly flaking of deposited conditioning agent whith continued use.

The present product is compatible with cationic surfactants and emulsifiers, such as quaternary ammonium salts; with non-ionic surfactants and emulsifiers such as alkyl or aryl polethyleneoxy alcohols; with amine oxide surfactants and emulsifiers; with alkylolamide surfactants; with amphoteric surfactants and emulsifiers such as "Miranols" and derivatives of aminoacetic acid and $\beta$-aminopropionic acid, and the like; and with surfactant and emulsifier betaines and betaine salts. It is also compatible with the common non-ionic cosmetic thickeners such as methyl cellulose, ethyl cellulose, hydroxyethyl cellulose and hydroxyethyl cellulose and hydroxypropyl cellulose.

Despite the fact that it is cationic, the present product is, quite surprisingly, compatible with certain anionic surfactants and emulsifiers such as salts of N-alkyl glycinates, N-alkyl sarcosinates N-alkyl $\beta$-aminopropionates, and alkyl or aryl polyethyleneoxy sulfates. But even more surprisingly, it can be made compatible with such anionic surfactants as alkyl sulfates and alkylaryl sulfonates, and the like, when these anionics are used in combination with amphoteric or betaine type surfactants and emulsifiers.

Therefore, the product of this invention can be used as a component not only of clear or opacified hair rinses, but of clear or opacified shampoos that can contain high-lathering surfactants.

The present product also has the property that, whether used as an additive in shampoos or in a hair rinse, it imparts a certain amount of "body" to the hair because of its substantive properties. Furthermore, when used as an additive in shampoos, it endows the wet hair with "cream rinse" properties because the wet hair is easily detangled and combed out. When it is used in a "setting lotion" or a "cream rinse", it allows the hair to hold a tight curl or "set" with greater efficiency and for longer periods of time than all of the other hair-conditioners tested. The product of our invention retains its hair conditioning properties in aqueous solution as well as in oil-in-water emulsions.

In addition to its hair conditioning properties in aqueous solution or in oil-in-water emulsions, the present product functions as a good emulsifier for water-in-oil emulsions. In this respect, it has been used as the sole emulsifier in water-in-oil emulsion with an oil content as high as 80%.

The following examples are illustrative of the present invention.

EXAMPLE 1

14.2 grams of 1,4-bis-dimethylamino-2-butene were mixed with 25 grams of isopropanol, and to it was added, with constant stirring, 12.5 grams of 1,4-dichloro-2-butene over a period of about 15 minutes (or at a rate which kept the mixture from overheating). After the exothermic reaction subsided, the reaction mixture was warmed on a steam bath for about one hour and cooled to room temperature. The precipitate, which was separated as the final product by filteration, weighted 18.7 grams. The same solid product was obtained when either acetone or 1,1,1-trichloroethane was used as the solvent instead of isopropanol.

EXAMPLE 2

14.2 grams of 1,4-bis-dimethylamino-2-butene was dissolved in about 40 grams of water, and to it was added 12.5 grams of 1,4-dichloro-2-butene over a period of 15 to 30 minutes, while constantly stirring the mixture. Since the reaction was exothermic, the dichlorobutene was added at a rate which kept the mixture from overheating. After addition, the reaction mixture was warmed on a steam bath until reaction was complete. The viscous reaction mixture contained about 40% active material.

This product was found to have the same hair conditioning properties as a 40% aqueous solution of the solid product that was made in Example 1. Such 40% aqueous solution shall hereafter be referred to as "Polymer A" in the formulations shown below, wherein all components are shown in percent by weight:

EXAMPLE 3

| Hair Shampoos | | | | |
|---|---|---|---|---|
| Components | Percent by weight | | | |
| "Polymer A" | 5 | 5 | 5 | 5 |
| "Miranol C 2M-SF" | 32 | — | — | — |
| "Maprofix 60S" | 10 | — | — | — |
| "Superamide GR" | 2 | 5 | — | — |
| "Maprofix RH" | — | 43 | — | 50 |
| "Meprofix 60N" | — | — | 25 | — |
| lauryl dimethyl betaine | — | — | 25 | — |
| "Sandopan TFL" | — | — | 4.2 | — |
| propylene glycol | 2 | 1 | 5 | — |
| deionized water | 48 | 45.6 | 35.7 | 44.5 |
| colorants, perfumes and other additives | 1 | 0.4 | 0.1 | 0.5 |
| pH | 5.5 | 6.8 | 5.8 | 6.1 |
| Viscosity (in centipoises) | 100 | 600 | 2040 | 11,000 |

EXAMPLE 4

| Clear Combing Aid and Hair Rinse | | | | |
|---|---|---|---|---|
| "Polymer A" | 2.5 | 6.95 | 6.95 | 6.9 |
| "Tergitol 15-S-12" | 0.1 | — | — | — |
| "Onyxide 500" | 0.1 | — | — | — |
| "Natrosol 250-HH" (3% aqueous solution) | — | 93 | — | — |
| "Klucel HF" (3% aqueous solution) | — | — | 93 | — |
| "Klucel LF" (3% aqueous solution) | — | — | — | 93 |
| propylene glycol | 10 | — | — | — |
| deionized water | 87.25 | — | — | — |
| colorant, perfumes and other additives | 0.05 | 0.05 | 0.05 | 0.1 |
| pH | 5.4 | 5.2 | — | 5.4 |
| Viscosity (centipoises) | 5 | >100,000 | >100,000 | 50 |

EXAMPLE 5

| Opaque Hair Rinse | |
|---|---|
| "Polymer A" | 5 |
| "Ammonyx 4" | 5 |
| "Onyxide 500" | 0.05 |
| "Peg 6000 Distearate" | 2.0 |
| "Onyxol 42" | 2.0 |
| cetyl alcohol | 0.5 |
| deionized water | 84.35 |
| colorants, perfumes and other additives | 1.1 |
| pH | 5.5 |
| Viscosity (centipoises) | 4200 |

EXAMPLE 6

| Pearlscent Hair Rinse and Hair Set | |
|---|---|
| "Polymer A" | 5 |
| "Peg 6000 Distearate" | 2.5 |
| "Onyxide 500" | 0.1 |
| deionized water | 92.35 |
| colorants, perfumes and other additives | 0.05 |
| pH | 5.7 |
| Viscosity (centipoises) | 610 |

EXAMPLE 7

| Clear Hair Setting Lotion | |
|---|---|
| "Polymer A" | 7.5 |
| deionized water | 92.49 |
| colorants, perfumes and other additives | 0.01 |
| pH | 5.5 |
| Viscosity (centipoises) | 5 |

EXAMPLE 8

| (Hair Cream (Water-In-Oil) Emulsion) | |
|---|---|
| "Polymer A" | 10 |
| mineral oil ("Drakeol #7") | 52 |
| beeswax | 5.6 |
| paraffin wax | 5.0 |
| petrolatum | 8.4 |
| cetyl alcohol | 3.0 |
| deionized water | 16.0 |
| Viscosity (centipoises) | 20,000 |

The proprietary components used in the above formulations and their sources are as follows:

"Miranol C-2M-SF" is an amphoteric surfactant, manufactured by Miranol Chemical Co., Irvington, N.J.

"Ammonyx 4", stearyl dimethyl benzyl ammonium chloride; "Maprofix 60S", sodium lauryl ether sulfate; "Maprofix RH", sodium lauryl ether sulfate/amphoteric blend; "Superamide 6R", coco diethanolamide; "Oynxide 500", 2-bromo-2-nitro-1,3-propanediol; and "Onyxol 42", stearyl diethanolamide; are all manufactured by the Onyx Chemical Company, Jersey City, N.J.

"Sandopan TFL", is a surfactant manufactured by the Sandoz Chemical Company, East Hanover, N.J.

"Natrosol 250-HH", hydroxyethyl cellulose; "Klucel HF", hydroxypropyl cellulose; and "Klucel LF", hydroxypropyl cellulose; are all manufactured by the Hercules Chemical Company, New York, N.Y.

"Peg 6000 Di-Stearate" is the di-stearate of polyethylene glycol having a molecular weight of 6000.

"Drakeol #7" is a mineral oil having a viscosity of 65/73 Saybolt, manufactured by Drake Refining Company, Butler, PA.

The products disclosed in Examples 3 to 7 were formulated for the purpose of showing how the product of the present invention may be used for the preparation of hair conditioning toiletries, but are not intended to be limitative with regard to the substitution of equivalent components of concentrations when used for certain specific requirements.

The product disclosed in Example 8 was not tested for its hair conditioning properties, but is included for the purpose of disclosing the totally unexpected property of the present product of being a good emulsifier for water-in-oil emulsions.

Formulations containing "Polymer A" in concentrations of less than one-half of one percent, with or without the usual additives found in hair conditioning preparations, exhibited none of the usual desirable properties expected of a hair conditioner. Tresses to which such preparations were applied exhibited extreme "drag" in wet combing and left a course feeling to the tresses after dry combing. However, formulations in which the concentrations of "Polymer A" was above one-half of one percent, but less than one percent, did impart a smooth conditioned feeling to the tresses after dry combing, although there was no reduction in "drag" upon wet combing.

Formulations in which "Polymer A" is present in a concentration of one percent and greater, and particularly where the concentration is between about 1 to about 10 percent, have all the desirable characteristics mentioned previously, while, as indicated above, at a concentration of 10 or above, the product is at least an effective emulsifier for water-in-oil emulsions. Therefore, the present product may be included in hair creams even without the presence of other emulsifiers.

The aqueous-system hair conditioning products having the formulae of Examples 3 to 7 were all prepared by substantially the same procedure. Such procedure is generally well-known in the art and is not intended to be limitative since modification for specific purposes may be made within the skill of the art. The procedure was as follows:

The water was heated to about 70° C.; then while maintaining constant agitation (stirring), the water-soluble materials (i.e. surfactants, humectants, thickeners, etc. and, finally, "Polymer A") were added slowly. Then the water-insoluble materials were added slowly, while still under agitation; after which the mixture was permitted to cool to about 40° C. Perfume and colorants were then added and the pH was adjusted with 20% citric acid, agitation being maintained throughout this period. Agitation was maintained until the mixture reached room temperature and was uniform.

The water-insoluble materials in Example 5 and 6 are the fatty acid ester "Peg 6000 Distearate" and the cetyl alcohol.

The water-in-oil system of Example 8 was also prepared by a procedure well known in the art but the specific procedure used is also not intended to be limitative since it may be modified for specific purposes within the skill of the art. The procedure used was as follows:

The water was heated to about 70° C. and the water-soluble components are dissolve therein. In a separate vessel, all of the water-insoluble components, which constitute the oil phase, were melted together and heated to a temperature slightly higher than the temperature of the aqueous solution. With constant agitation (stirring), the aqueous solution was added in small increments to the oil phase. Agitation was continued while the mixture cooled spontaneously to about 40° C. Perfumes and colorants were then optionally added, if desired, and stirring was discontinued when the mixture was uniform and at room temperature.

The water-insoluble oil phase in Example 8 comprises the mineral oil, beeswax, paraffin wax, petrolatum and cetyl alcohol.

The invention claimed is:

1. A method of conditioning the hair which comprises applying to said hair a conditioningly effective amount of an emulsion containing a condensation product of 1,4-dichloro-2-butene and 1,4-bis-dimethylamino-2-butene in molar ratio of from about 1:2 to about 2:1.

2. The method of claim 1 wherein said condensation product is applied to hair while present in the emulsion in an amount of from about 0.5 percent to about 10.0 percent by weight of the total composition.

3. The method of claim 2 in which said emulsion also contains a surface-actively effective amount of a member selected from the group consisting of non-ionic, cationic, anionic, amphoteric, and betaine surfactants, and mixtures thereof.

4. The method of claim 3 in which said emulsion is an oil-in-water emulsion.

* * * * *